United States Patent [19]

Pettit et al.

[11] Patent Number: 5,780,588
[45] Date of Patent: Jul. 14, 1998

[54] ELUCIDATION AND SYNTHESIS OF SELECTED PENTAPEPTIDES

[75] Inventors: George R. Pettit, Paradise Valley; Jayaram K. Srirangam, Tempe, both of Ariz.

[73] Assignee: Arizona Board of Regents, Tempe, Ariz.

[21] Appl. No.: 9,296

[22] Filed: Jan. 26, 1993

[51] Int. Cl.$^6$ .................................................. A61K 38/08
[52] U.S. Cl. ............................ 530/330; 514/17; 514/18
[58] Field of Search ........................ 514/15, 17; 530/330, 530/323

[56] References Cited

PUBLICATIONS

Jacobsen, *J. Natl Cancer Inst 83*, 1672, 1991.
Bai *Biochem Pharmacol, 40*, 1859, 1990.

*Primary Examiner*—Robert J. Hill, Jr.
*Assistant Examiner*—David Lukton
*Attorney, Agent, or Firm*—Richard R. Mybeck

[57] ABSTRACT

The sea hare *Dolabella auricularia* has yielded many structurally distinct peptides which possess antineoplastic activity. Presently the compound denominated "dolastatin 10" represents the most important of such peptides because of its demonstrated potential as an anticancer drug.

The present invention relates to the systematic creation of five unique pentapeptides by selectively coupling a tripeptide-trifluoroacetate salt with a preselected dipeptide-trifluoroacetate salt which provide active molecules capable of emulating the measured therapeutic effect of dolastatin 10. The pentapeptides hereof have the structure shown below:

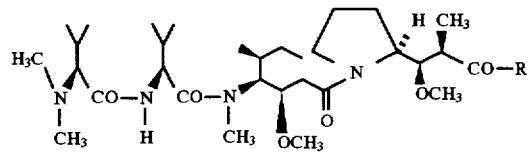

wherein R is selected from the following group of substituents:

a)

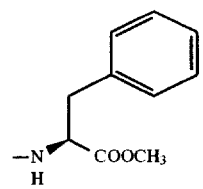

b)

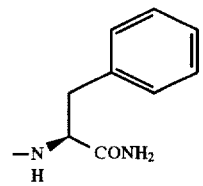

c)

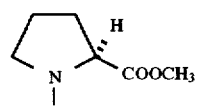

d)

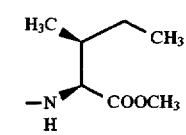

e)

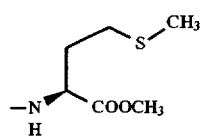

19 Claims, No Drawings

5,780,588

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( v i ) ORIGINAL SOURCE: synthesis ( i x ) FEATURE:
        ( A ) NAME/KEY: [2S-[1[1R*(R*),2S],2R*[1S*,2S*]]]-
            N,N-dimethyl- L-valyl-N-[2-methoxy-4-[2-[1-methoxy-2-
            methyl-3-oxo- 3-[[2-phenyl-1-carbomethoxy]ethyl]
            amino]propyl]-1-pyrrolidinyl-1-(methylpropyl)-4-
            oxobutyl]- N-methyl-L-valinamide
        ( B ) IDENTIFICATION METHOD: by experiment using
            high resolution nuclear magnetic resonance and mass
            spectral techniques
        ( C ) OTHER INFORMATION: This pentapeptide is
            cell growth inhibitory peptide derivative ( x i ) SEQUENCE DESCRIPTION: SEQ ID NO: 1:

Xaa Val Xaa Xaa Xaa ( 2 ) INFORMATION FOR SEQ ID NO: 2:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( v i ) ORIGINAL SOURCE: synthesis ( i x ) FEATURE:
        ( A ) NAME/KEY: [2S-[1[1R*(R*),2S],2R*[1S*,2S*]]]-
            N,N-dimethyl- L-valyl-N-[2-methoxy-4-[2-[1-methoxy-2-
            methyl-3-oxo- 3-[[2-phenyl-1-aminocarboxy]ethyl]
            amino]propyl]-1-pyrrolidinyl-1-(methylpropyl)-4-
            oxobutyl]- N-methyl-L-valinamide
        ( B ) IDENTIFICATION METHOD: by experiment using
            high resolution nuclear magnetic resonance and mass
            spectral techniques
        ( C ) OTHER INFORMATION: This pentapeptide is
            cell growth inhibitory peptide derivative ( x i ) SEQUENCE DESCRIPTION: SEQ ID NO: 2:

Xaa Val Xaa Xaa Xaa ( 2 ) INFORMATION FOR SEQ ID NO: 3:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( v i ) ORIGINAL SOURCE: synthesis ( i x ) FEATURE:
        ( A ) NAME/KEY: [2S-[1[1R*(R*),2S],2R*[1S*,2S*]]]-
            N,N-dimethyl- L-valyl-N-[2-methoxy-4-[2-[1-methoxy-2-
            methyl-3-oxo- 3-[O-methyl-L-prolyl]propyl]-1-
            pyrrolidinyl- 1-(methylpropyl)-4-oxobutyl]-N-methyl-
            L- valinamide
        ( B ) IDENTIFICATION METHOD: by experiment using
            high resolution nuclear magnetic resonance and mass
            spectral techniques
        ( C ) OTHER INFORMATION: This pentapeptide is
            cell growth inhibitory peptide derivative ( x i ) SEQUENCE DESCRIPTION: SEQ ID NO: 3:

Xaa Val Xaa Xaa Xaa ( 2 ) INFORMATION FOR SEQ ID NO: 4:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide ( i i i ) HYPOTHETICAL: no ( i v ) ANTI-SENSE: no ( v i ) ORIGINAL SOURCE: synthesis ( i x ) FEATURE:
        ( A ) NAME/KEY: [2S-[1[1R*(R*),2S],2R*[1S*,2S*]]]-
            N,N-dimethyl- L-valyl-N-[2-methoxy-4-[2-[1-methoxy-2-
            methyl-3-oxo- 3-[O-methyl-L-isoleucyl]propyl]-1-
            pyrrolidinyl- 1-(methylpropyl)-4-oxobutyl]-N-methyl-
            L- valinamide
        ( B ) IDENTIFICATION METHOD: by experiment using
            high resolution nuclear magnetic resonance and mass
            spectral techniques
        ( C ) OTHER INFORMATION: This pentapeptide is
            cell growth inhibitory peptide derivative ( x i ) SEQUENCE DESCRIPTION: SEQ ID NO: 4:

Xaa Val Xaa Xaa Xaa ( 2 ) INFORMATION FOR SEQ ID NO: 5:

( i ) SEQUENCE CHARACTERISTICS:
        ( A ) LENGTH: 5 amino acid residues
        ( B ) TYPE: amino acid
        ( D ) TOPOLOGY: linear ( i i ) MOLECULE TYPE:
        ( A ) DESCRIPTION: Linear pentapeptide

```
(iii) HYPOTHETICAL: no (iv) ANTI-SENSE: no (vi) ORIGINAL SOURCE: synthesis (ix) FEATURE:
    (A) NAME/KEY: [2S-[1[1R*(R*),2S],2R*[1S*,2S*]]]-
        N,N-dimethyl- L-valyl-N-[2-methoxy-4-[2-[1-methoxy-2-
        methyl-3-oxo- 3-[[3-thiomethyl-1-(2-carbomethoxy)
        ethyl]amino]propyl]-1-pyrrolidinyl-1-(methylpropyl)-
        4-oxobutyl]-N-methyl-L-valinamide
    (B) IDENTIFICATION METHOD: by experiment using
        high resolution nuclear magnetic resonance and mass
        spectral techniques
    (C) OTHER INFORMATION: This pentapeptide is
        cell growth inhibitory peptide derivative (xi) SEQUENCE DESCRIPTION: SEQ ID NO: 5:

Xaa  Val  Xaa  Xaa  Xaa
```

ELUCIDATION AND SYNTHESIS OF SELECTED PENTAPEPTIDES

Financial assistance for this project was provided by U.S. Government Grant Number OIG-CA44344-01A1-2: the United Statess Government may own certain rights to this invention.

This invention relates generally to the field of antineoplastic compounds, and more particularly to the elucidation and synthesis of selected pentapeptides prepared by coupling dipeptide salts with the known tripeptide-trifluoroacetate salt. More particularly, the present invention relates to the synthesis of five pentapeptides by the coupling of a tripeptide-trifluoroacetate salt with the respective dipeptide-trifluoroacetate salt, which was itself prepared by the coupling of dolaproine with the respective amino acid. This coupling results in compounds which are found to exhibit effective antineoplastic activity against various human cancerous tumor cell lines.

BACKGROUND OF THE INVENTION

Ancient marine invertebrate species of the Phyla Bryozoa, Molluska, and Porifera have been well established in the oceans for over one billion years. Such organisms have undergone trillions of biosynthetic reactions in their evolutionary chemistry to reach their present level of cellular organization, regulation and defense.

For example, marine sponges have changed minimally in physical appearance for nearly 500 million years. This suggests a very effective chemical resistance to evolution in response to changing environmental conditions over that period of time. Recognition of the potential for utilizing this biologically potent marine animal for medicinal purposes was recorded in Egypt about 2,700 BC and by 200 BC sea hare extracts were being used in Greece for their curative affect. This consideration along with the observation that marine animals, e.g. invertebrates and sharks, rarely develop cancer led to the systematic investigation of marine animal and plant anticancer compounds.

By 1968 ample evidence had been obtained, based on the U.S. National Cancer Institute's (NCI) key experimental cancer study systems, that certain marine organisms could provide new and antineoplastic and/or cytotoxic agents and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data approaches ten million dollars per compound. As such, economics dictate that such a huge investment will be made only when there is a reasonable opportunity for it to be recovered. Absent such opportunity, there will be no investment and the research involving the discovery of these potentially life saving compounds will cease. Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and has been accepted in scientific circles. The protocol, and the established statistical means for analyzing the results obtained by the standardized testing are fully described in the literature. See: Boyd, Dr. Michael R., *Principles & Practice of Oncology*. PPO Updates, Volume 3, Number 10, October 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports*, Vol. 81, No. 14, Page 1088, Jul. 14, 1989 for a description of the methods of statistical analysis. Both of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The impairment of human cancerous tumor growth is utilitarian in that it relieves these conditions, thereby allowing the human thus affected to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive for further research.

The recognition of antineoplastic and tumor inhibiting activity as demonstrated by accepted NCI criteria as "utility" can promote research efforts in the United States and is unequivocally essential if those efforts are to obtain even a modest modicum of success.

BRIEF SUMMARY OF THE INVENTION

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from Indian Ocean sea hare *Dolabella auricularia* represent excellent leads for synthetic modification. The very productive sea hare *Dolabella auricularia* has produced a number of structurally distinct peptides with excellent antineoplastic activity. Presently Dolastatin 10, a linear pentapeptide represents the most important member and is a potentially useful antineoplastic agent. Dolastatin 10 shows one of the best antineoplastic activity profiles against various cancer screens presently known.

This research has led to an effective method for the synthesis of new and very potent anti-cancer pentapeptides related in structure to Dolastatin 10. The present invention involves the structure and synthesis of five such pentapeptides as shown below.

Accordingly, the primary object of the subject invention is the synthesis of five pentapeptide derivatives of dolastatin 10 which exhibit effective antineoplastic activity against various human cancerous tumor cell lines.

Another object of the subject invention is the synthesis of pentapeptide derivatives of dolastatin 10 through the coupling of respective tripeptide and dipeptide trifluoroacetate salts, wherein the dipeptide salt was prepared by the coupling of dolaproine and the respective amino acid.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from Indian Ocean sea hare *Dolabella auricularia* represent excellent leads for synthetic modification. The very productive sea hare *Dolabella auricularia* has produced a number of structurally distinct peptides with excellent antineoplastic activity. Presently Dolastatin 10, a linear pentapeptide represents the most important member and is a potentially useful antineoplastic agent. Dolastatin 10 shows one of the best antineoplastic activity profiles against various cancer screens presently known. Recently the total synthesis and absolute configuration of this structurally unique and biologically active peptide was reported. This compound has been tested in vivo and demonstrated significant activity, as shown below.

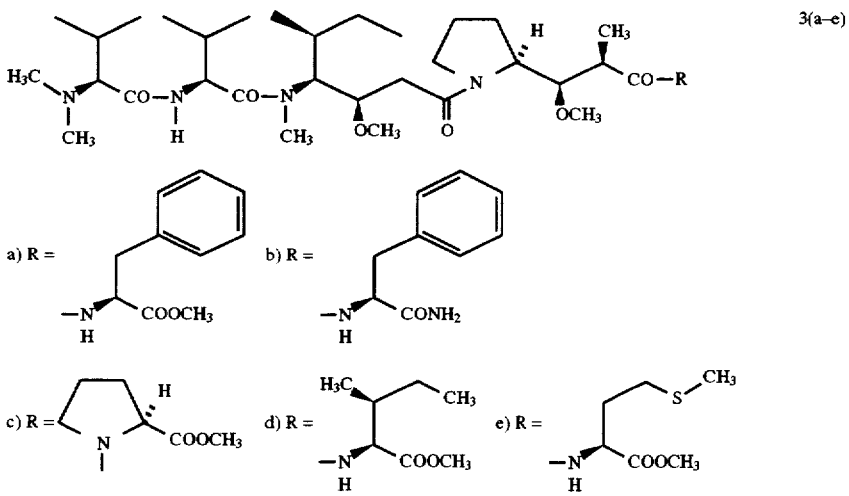

3(a-e)

| Experimental Anticancer Activity of Dolastatin 10 in Murine in vivo Systems. T/C (µg/kg) | |
| --- | --- |
| P388 Lymphocytic Leukemia | LOX Human Melanoma Xenograph to (Nude Mouse) |
| toxic (13.0) | |
| 155 and 17% cures (6.5) | toxic (52) |
| 146 and 17% cures (3.25) | 301 and 67% cures (26) |
| 137 (1.63) | 301 and 50% cures (13) |
| L1210 Lymphocytic Leukemia | 206 and 33% cures (6.5) |
| 152 (13) | 170 and 17% cures (3.25) |
| 135 (6.5) | LOX in separate experiments |
| 139 (3.25) | 340 and 50% cures (43) |
| 120 (1.63) | 181 and 33% cures (26) |
| B16 Melanoma | 192 (15) |
| 238 and 40% cures (11.11) | 138 and 17% cures (9.0) |
| 182 (6.67) | Human Mammary Xenograph |
| 205 (4.0) | Nude Mouse |
| 171 (3.4) | Toxic (26) |
| 142 (1.44) | 137 (13) |
| M5076 Ovary Sarcoma | 178 (6.25) |
| toxic (26) | OVCAR-3 Human Ovary Xenograph |
| 166 (13) | Nude Mouse |
| 142 (6.5) | 300 (40) |
| 151 (3.25) | |
| MX-1 Human Mammary Xenograft (Tumor Regression) | |
| 14 (52) | |
| 50 (26) | |
| 61 (13) | |
| 69 (6.25) | |

Dolastatin 10 has also been tested against a minipanel from the NCI Primary screen. These results appear below, showing the amount of Dolastatin 10 required to attain $GI_{50}$ in µg/ml, against the cell lines set forth below.

$$\frac{OVCAR-3}{9.5 \times 10^{-7}} (A) \frac{SF\ 295}{7.6 \times 10^{-8}} (B) \frac{A498}{2.6 \times 10^{-5}} (C)$$

$$\frac{NCI-H460}{3.4 \times 10^{-6}} (D) \frac{KM20L2}{4.7 \times 10^{-6}} (E) \frac{SK-MEL-5}{7.4 \times 10^{-6}}$$

From the foregoing, it can be seen that the in vitro activity of dolastatin 10 in the primary screen has been confirmed by in vivo animal tests.

For the compounds disclosed in this application, the in vitro tests disclosed above are reasonably accurate predictors of anticancer activity, and not mere indicators of the desirability for further testing.

These newly discovered pentapeptide compounds (3a–3e), related to Dolastatin 10, are formed by the coupling of the respective dipeptide-fluoroacetate salts (2a–2e) with the known tripeptide-trifluoroacetate salt (4). The dipeptides (1a–1e) were in turn prepared by coupling dolaproine (5) with the respective amino acids. All compounds were characterized (physical and spectroscopic data) and tested against the murine lymphocytic P388 leukemia cell line as well as six major human cancer cell lines. The remarkable cancer cell growth inhibitory data are shown in Table 1.

TABLE 1

Potent inhibition of Cancer cell lines by pentapeptides 3a-e

| TEST | | | PENTAPEPTIDE | | | | |
| --- | --- | --- | --- | --- | --- | --- | --- |
| µg/ml | CELL TYPE | CELL LINE | 3a | 3b | 3c | 3d | 3e |
| $ED_{50}$ | MOUSE LEUKEMIA | P388 | 0.0667 | 0.0195 | 0.0088 | 0.000441 | 0.000389 |
| GI-50 | Ovarian | OVCAR-3 | <0.0001 | 0.0076 | <0.0001 | <0.0001 | <0.0001 |
| | CNS | SF-295 | <0.0001 | 0.00085 | <0.0001 | <0.0001 | <0.0001 |
| | Renal | A498 | <0.0001 | 0.00097 | <0.0001 | <0.0001 | <0.0001 |
| | Lung-NSC | NCI-H460 | <0.0001 | 0.000095 | <0.0001 | <0.0001 | <0.0001 |
| | Colon | KM20L2 | <0.0001 | <0.0001 | <0.0001 | <0.0001 | <0.0001 |
| | Melanoma | SK-MEL-3 | <0.0001 | 0.00017 | <0.0001 | <0.0001 | <0.0001 |
| TGI | Ovarian | OVCAR-3 | 0.0011 | 0.0037 | <0.0001 | <0.0001 | <0.0001 |
| | CNS | SF-295 | 0.00017 | 0.049 | 0.0024 | 0.17 | 0.056 |
| | Renal | A498 | 0.0029 | 0.0062 | 0.0054 | <0.0001 | >1 |
| | Lung-NSC | NCI-H460 | 0.011 | 0.011 | 0.0013 | 0.00088 | 0.13 |
| | Colon | KM20L2 | 0.0011 | 0.019 | 0.0022 | <0.0001 | 0.00015 |
| | Melanoma | SK-MEL-3 | 0.00068 | 0.012 | <0.0001 | <0.0001 | >1 |
| LC-50 | Ovarian | OVCAR-3 | >1 | 0.066 | >1 | 0.043 | >1 |
| | CNS | SF-295 | >1 | >1 | >1 | >1 | >1 |
| | Renal | A498 | >1 | >1 | >1 | >1 | >1 |
| | Lung-NSC | NCI-H460 | >1 | >1 | >1 | >1 | >1 |
| | Colon | KM20L2 | >1 | 0.083 | >1 | >1 | >1 |
| | Melanoma | SK-MEL-3 | >1 | >1 | >1 | >1 | >1 |

The human cancer cell lines results shown for pentapeptides 3a–e in Table I illustrate remarkably patent and selective activity against human ovary, CNS (brain), kidney, lung, colon and melanoma type cancers. In this respect, each compound parrots a pattern previously discovered for Dolastatin 10 and as such is reasonably expected to generate in vivo data results comparable to those reported above for Dolastatin 10.

The scheme and structures of these pentapeptides appear below:

96%); m.p=125° C.; $[\alpha]_D^{25}=-15.1°$ (c 0.41, CHCl$_3$); IR(thin film: 3314, 2974, 2934, 2878, 1748, 1692, 1663, 1537, 1456, 1400, 1366, 1173, 1101 and 700; $^1$H NMR (300 MHz, CDCl$_3$):1.163(d, J=7.0 Hz, 3H, CH$_3$), 1.4816(s, 9H, t-Bu), 1.624–1.850(m, 4H, 2×CH$_2$), 2.25–2.45(m, 1H, CHCO), 3.045(dd, J=13.9 and 7.8 Hz, 1H, ½ CH$_2$-Ph), 3.175(dd, J=13.8 and 5.55 Hz, 1H, ½ CH$_2$-Ph), 3.3642(s, 3H, OCH$_3$), 3.3701(s, 3H, OCH$_3$), 3.50–3.60(m, 1H, CH–OCH$_3$), 3.7422(m, 2H, CH$_2$—N), 3.85(m, 1H, pro CH—N), 4.80(m, 1H, phe CH—N), 6.10, 6.75(m, 1H, NH) and 7.10–7.32(m, 5H, Ph); MS: m/z 416[M—CH$_3$OH], 375, 316, 264, 210,

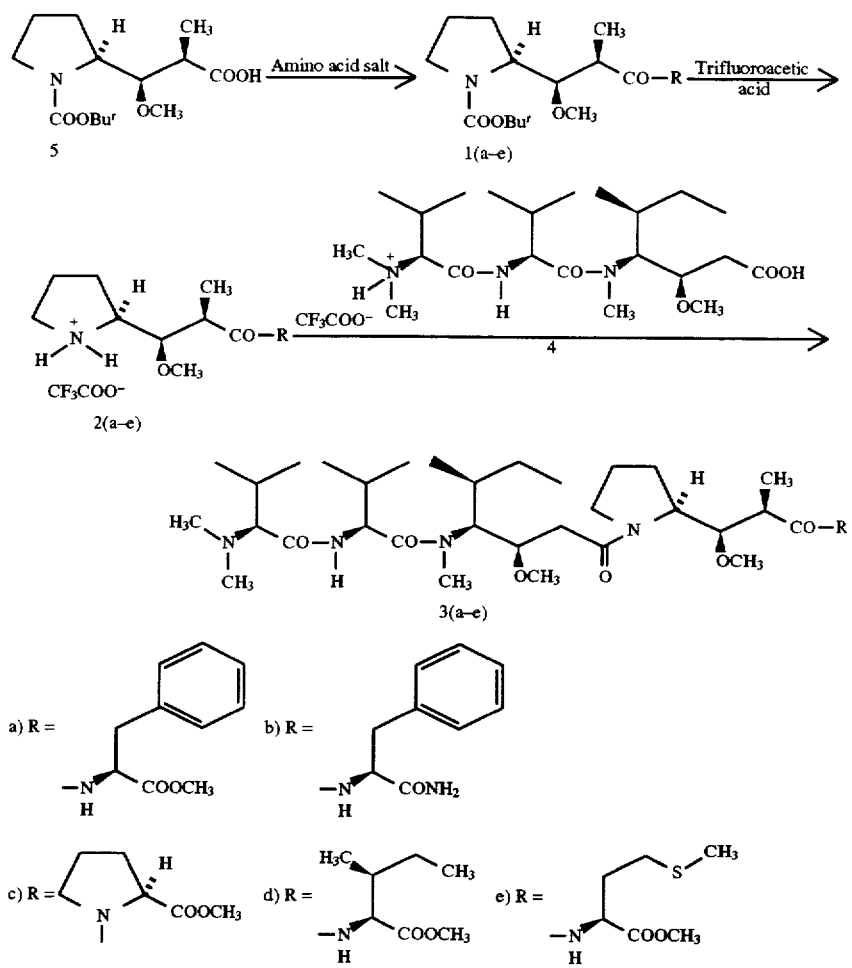

SCHEME 1

General Procedure for the Synthesis of Dipeptides (1a–1e)

To a solution of dolaproine tfa salt (1 mmol) and the amino acid salt (1 mmol) in dry dichloromethane (2 ml), cooled to ice-bath temperature under an argon atmosphere was added dry triethylamine (3 mmol) followed by diethylcyanophophonate (1.1 mmol). The solution was stirred at the same ice bath temperature for 1–2 hr. The salts that precipitated were collected, the solvent was evaporated (under reduced pressure) and the residue chromatographed over a SILICA GEL column with solvents noted to obtain the respective dipeptides.

i) Boc-Dap-Phe-OCH$_3$ (1a):

Chromatographic separation on a SILICA GEL column with 3:1 hexane-acetone as the eluent resulted in the required dipeptide as a thick oil. Crystallization from ether-hexane gave sparkling crystals of the pure compound (1a, 170, 114(100%) and 70. Anal. Found: H: 8.12, N: 6.20. C$_{24}$H$_{36}$N$_2$O$_6$ requires H:8.09, N: 6.25.

ii) Boc-Dap-Phe-Nh$_2$ (1b):

Chromatographic purification using a SILICA GEL column with 1:1 hexane-acetone as the eluent gave the required dipeptide as a crystalline solid. Recrystallization from acetone gave sparkling crystals of the pure compound (1b, 65%); m.p.=199°–200° C. (acetone); $[\alpha]_D^{25}=-40°$ (c 0.15, CHCl$_3$); IR(thin film): 3302, 3198, 2974, 2934, 2878, 1669, 1539, 1456, 1404, 1366, 1169, 1111 and 700; $^1$H NMR (300 MHz, CDCl$_3$): 1.019(brs, 3H, CH$_3$), 1.426(s, 9H, t-Bu), 1.55–1.90(m, 4H, 2×CH$_2$), 2.30(quintet, 1H, CH—CO), 3.00–3.25(m, 3H, CH$_2$—N, CH—OCH$_3$), 3.349(s, 3H, OCH$_3$), 3.60–3.75(m, 1H, pro CH—N), 4.60–4.80(m, 1H, phe CH—N), 5.30(brs, 1H, NH), 6.287(d, J=7.2 Hz, 1H, NH), 6.90 (brm, 1H, NH) and 7.164–7.306(m, 5H, C$_6$H$_5$);

MS: m/z 433(M⁺), 401(M—MeOH), 360, 301, 247, 232, 210, 170, 154, 138, 114 and 70(100%). Anal. Found: C: 63.75, H:8.18, N:9.62. $C_{23}H_{35}N_3O_5$ requires C: 63.72, H: 8.14, N: 9.69.

iii) Boc-Dap-Pro-OCH₃ (1c):

Chromatographic separation on a SILICA GEL column with 3:2 hexane-acetone as the eluent gave the required dipeptide as a thick oil (1c, 92%); $[\alpha]_D^{25}=-101.5°$ (c 0.2, CHCl₃); IR(neat): 2974, 2880, 1748, 1692, 1647, 1398, 1366, 1171 and 1098; ¹H NMR (300 MHz, CDCl₃): 1.222(d, J=7.0 Hz, 3H, CH₃), 1.440(s, 9H, t-Bu), 1.65–2.20(m, 8H, 4×CH₂), 2.60–2.70(m, 1H, CH—CO), 3.10–3.22(m, 1H, CH—OCH₃), 3.417(s, 3H, CH₃), 3.45–3.65(m, 4H, 2×CH₂—N), 3.675(s, 3H, OCH₃), 3.74–3.83(m, 1H, CH—N) and 4.447(dd, J=8.55 and 3.5 Hz, 1H, CH—COOCH₃). HRFABMS: m/z 399.24880|M+H|⁺. $C_{20}H_{35}N_2O_6$ requires 399.24951.

iv) Boc-Dap-Ile-OCH₃ (1d):

Chromatographic purification on a SILICA GEL column with 3:2 hexane-ethyl acetate as the eluent yielded the required dipeptide as an oily liquid (1d, 72%); m.p.=76°–77° C. (acetone); $[\alpha]_D^{25}=-28.2°$ (c 0.17, CHCl₃); IR(thin film): 3325, 2971, 2936, 2878, 1746, 1694, 1667, 1530, 1478, 1398, 1254, 1175, 1105, 868 and 774; ¹H NMR (300 MHz, CDCl₃) 0.882(d, J=6.9 Hz, 3H, C$\underline{H}_3$—CH), 0.9012(t, J=7.4 Hz, 3H, C$\underline{H}_3$—CH₂), 1.05–1.24(m, 5H, CH₃, C$\underline{H}_2$—CH₃) 1.4526(s, 9H, t-Bu), 1.65–2.00(m, 5H, 2×CH₂, C$\underline{H}$—CH₂), 2.30–2.50(m, 1H, CH—CO), 3.18–3.28((m, 1H, C$\underline{H}$—OCH₃), 3.422(s, 3H, OCH₃, 3.48–3.60(m, 1H, pro C$\underline{H}$—N), 3.699(s, 3H, OCH₃), 3.72–3.82(m, 1H, ½ CH₂—N), 3.88–3.98(m, 1H, ½ CH₂—N), 4.44–4.58(m, 1H, ile CH—N) and 6.15, 6.7(m, 1H, NH); MS: m/z 382(M—MeOH), 341, 282, 245, 230, 210, 170, 114, 70(100%) and 57. Anal. Found: C: 61.06, H: 9.25, N: 6.64. $C_{21}H_{38}N_2O_6$ requires C: 60.84, H: 9.24, N: 6.76.

v) Boc-Dap-Met-OCH₃ (1e):

Chromatographic separation on a SILICA GEL column using 3:2 hexane-acetone as the eluent gave the required dipeptide as a solid (1e, 83%); m.p.=68°–70° C.; $[\alpha]_D^{25}=-27.6°$ (c, 0.59, CHCl₃); IR(neat): 3312, 2974, 2934, 2878, 1748, 1692, 1663, 1539, 1398, 1366, 1256, 1171, 1115, 866 and 774; ¹H NMR (CDCl₃): 1.223(brs, 3H, CH—CH₃), 1.441(brs, 9H, t-Bu), 1.6–1.2(m, 6H, 3×CH₂), 2.070 (s, 3H, S—CH₃), 2.3–2.55(m, 3H, CH₂—S, CH—CO), 3.15–3.35 (m, 2H, N—CH₂), 3.420 (s, 3H, OCH₃), 3.55(m, 1H, CH—OCH₃), 3.716(brs, 3H, COOCH₃), 3.85–4.0(m, 1H, pro CH—N), 4.6(brm, 1H, met CH—N ), 6.3(brm, 1H, NH); MS (m/z): 432 (M⁺), 400, 359, 258, 210, 170, 114(100%). Anal. Found: C: 55.35, H: 8.33, N: 6.53, S: 7.23. $C_{20}H_{36}N_2O_6$ S requires C: 55.53, H: 8.39, N: 6.48, S: 7.41.

Synthesis of phenylalanine amide trifluoroacetate salt

To a solution of t-boc-phenylalanine amide (3, 80 mg, 0.303 mmol) in dichloromethane (0.5 ml) was added trifluoroacetic acid (1 ml) at ice-bath temperature and the solution was stirred at the same temperature for 1.5 hr. under argon atmosphere. The solvents were removed under reduced pressure and the residue taken into toluene and toluene also removed under reduced pressure to obtain a white solid of the trifluoroacetate salt (80 mg, 95%); ¹H NMR (DMSO-d₆, 300 MHz): 2.95–3.10(m, 2H, C₆H₅—CH₂), 3.3209(brs, 2H, NH₂), 3.9408(brs, 1H, CH—N), 7.236–7.317(m, 5H, C₆H₅) and 7.528, 7.862, 8.150(brs, 3H, NH₃⁺).

DEPROTECTION OF DIPEPTIDES 1a–e WITH TRIFLUOROACETIC ACID-GENERAL PROCEDURE

To a solution of the Boc-protected dipeptide (1 mmol) in dry dichloromethane (2 ml, cooled to ice-bath temperature, under an argon atmosphere) was added trifluoroacetic acid (2 ml) and the solution was stirred at the same temperature for 1–2 hr. After removing the solvent under reduced pressure, the residue was dissolved in toluene and solvent was again removed under reduced pressure. The latter operation was repeated to remove all the trifluoroacetic acid. The residue was dried (in vacuo) to obtain the trifluoroacetate salts of the respective dipeptides. Wherever possible, the trifluoroacetate salts were characterized from spectral data and physical constants recorded.

Synthesis of Dap-Phe-OCH₃ Tfa (2a)

After removing toluene under reduced pressure, the residue obtained as a thick oily mass was triturated with ether to obtain the trifluoroacetate salt (2a, quantitative) as a colorless crystalline solid: IR(thin film): 3275, 2928, 1744, 1674, 1541, 1456, 1202, 1132 and 721; ¹H NMR (300 MHz, CDCl₃): 1.107(brs, 3H, CH₃), 1.60–2.10 (m, 4H, 2×CH₂), 2.60 (m, 1H, CHCO), 2.90–3.00 (m, 2H, CH₂—Ph), 3.10–3.35(m, 3H, C$\underline{H}$—OCH₃, CH₂—N), 3.209(s, 3H, OCH₃), 3.40–3.55(m, 1H, pro CH—N), 3.712(s, 3H, COOCH₃), 4.75(m, 1H, phe CH—N), 7.106(m, 1H, NH), 7.124–7.324(m, 5H, Ph) and 8.7(m, 1H, NH); HRFABMS: m/z 349.21350(100%, cation); $|C_{19}H_{29}N_2O_4|^+$ requires 349.21273.

Synthesis of Dap-Phe-NH₂ Tfa (2b)

Removal of toluene under reduced pressure left the trifluoroacetate salt (2b, 97%) as a colorless solid.

Synthesis of Dap-Pro-OCH₃ Tfa (2c)

After removing toluene under reduced pressure, the residue obtained as a thick oily mass was triturated with ether to obtain the trifluoroacetate salt (2c, 99%) as a colorless crystalline solid: IR(thin film): 2980, 2890, 1746, 1680, 1626, 1437, 1287, 1200, 1094, 799 and 721; ¹H NMR (300 MHz, CDCl₃): 1.307(d, J=6.9 Hz, 3H, CH₃), 1.85–2.30(m, 8H, 4×CH₂), 2.85(m, 1H, CH—CO), 3.20–3.40(m, 1H, CH—OCH₃), 3.485(s, 3H, CH₃), 3.35–3.75(m, 3H, CH—N, CH₂—N), 3.687(s, 3H, COOOCH₃), 4.165(m, 2H, CH₂—N⁺), 4.442(m, 1H, CH—N⁺) and 8.008(m, NH). HRFABMS: m/z 299.19770(100%, cation); $|C_{15}H_{27}N_2O_4|^+$ requires 299.1971.

Synthesis of Dap-Ile-OCH₃ Tfa (2d)

After removing toluene under reduced pressure, the residue obtained as a thick oily mass was triturated with ether to obtain the trifluoroacetate salt (2d, 97%) as a gummy mass: IR(thin film): 3289, 2969, 2884, 1744, 1674, 1541, 1458, 1383, 1202, 1136, 833, 799 and 721; ¹H NMR (300 MHz, CDCl₃): 0.88(brs, 3H, C$\underline{H}_3$), 1.884(t, J=6.7 Hz, 3H, C$\underline{H}_3$—CH₂), 1.209(d, J=6.8 Hz, C$\underline{H}_3$—CH), 1.10–1.50(m, 2H, CH₂), 1.80–2.20(m, 5H, 2×CH₂, CH₃—C$\underline{H}$), 2.707(m, 1H, CH—CO), 3.10—3.41(m, 2H, CH₂—N), 3.470(s, 3H, OCH₃), 3.60–3.70(M, 1H, C$\underline{H}$—OCH₃), 3.48–3.85–3.90(m, 1H, pro C$\underline{H}$—N), 3.702(s, 3H, COOCH₃), 4.43(dd, J=7.5 and 5.4 Hz, 1H, ile CH—N), 6.926(d, J=7.9 Hz, 1H, NH), 8.8(m, 1H, ½ NH₂) and 10(m, 1H, ½ NH₂); MS: HRFAB: m/z 315.22890(100%. Cation); $|C_{16}H_{31}N_2O_4|^+$ requires 315.22838.

Synthesis of Dap-Met-OCH₃ Tfa (2e)

Removal of toluene under reduced pressure left the trifluoroacetate salt (2e, quantitative) as a gummy mass.

SYNTHESIS OF PENTAPEPTIDES 3a–e—GENERAL PROCEDURE

To a solution of the tripeptide tfa salt (4, 1 mmol) and the dipeptide tfa salt (1 mmol) in dichloromethane (2 ml, ice-bath and under argon) was added dry triethylamine (3 mmol) followed by diethylcyanophosphonate (1.1 mmol). The solution was stirred at the same temperature for 1–2hr. After removing solvent under reduced pressure the residue was chromatographed on a SILICA GEL column using the solvent system given below as eluents to obtain the respective pentapeptides (3a–e)

Dov-Val-Dil-Dap-Phe-OCH$_3$ (3a)

Chromatographic separation on a SILICA GEL column with 3:4 hexane-acetone as the eluent gave the required pentapeptide(3a, 87%); m.p.=80°–83° C.; $[\alpha]_D^{25}$=–35.3° (c 0.34, CHCl$_3$); IR(thin film): 3298, 2963, 2934, 2876, 2830, 2787, 1748, 1622, 1532, 1454, 1379, 1269, 1200, 1099, 1038, 737 and 700; MS: m/z 759(M$^+$), 716, 481, 449, 433, 227, 186, 154, 128, 100(100%), 85 and 70. Anal. Found: C: 64.91, H: 9.33, N: 8.97. C$_{41}$H$_{69}$N$_5$O$_8$ requires C: 64.71, H: 9.15, N: 9.22.

Dov-Val-Dil-Dap-Phe-NH$_2$ (3b)

Chromatographic separation on a SILICA GEL column with 1:3 hexane-acetone as the eluent resulted in the required pentapeptide as colorless powder (3b, 99%); m.p.= 111°–113° C.; $[\alpha]_D^{25}$=–42° (c 0.25, CHCl$_3$); IR(thin film): 3304, 3138, 3054, 2965, 2934, 2876, 2830, 2787, 1622, 1541, 1499, 1423, 1371, 1306, 1252, 1202, 1171, 1098, 1038, 756, 735 and 696; MS: m/z 744(M$^+$), 701, 669, 519, 481, 418, 227, 206, 186, 170, 154, 128 and 114.

Dov-Val-Dil-Dap-Pro-OCH$_3$ (3c)

Chromatographic purification using a SILICA GEL column with 1:3 hexane-acetone as the eluent yielded the required pentapeptide as colorless powder (3c, 69%); m.p.= 75°–77° C.; $[\alpha]_D^{25}$=–52.7° (c 0.11, CHCl$_3$); IR(thin film): 3293, 2963, 2876, 2830, 2789, 1750, 1624, 1422, 1385, 1273, 1198, 1096, 1040 and 733; MS: m/z 709(M$^+$), 666, 581, 481, 449, 412, 383, 369, 297, 255, 227(100%), 199, 186, 170 and 155. Anal. Found: C: 62.51, H: 9.61, N: 9.72. C$_{37}$H$_{67}$N$_5$O$_8$ requires C: 62.59, H: 9.51, N: 9.87.

Dov-Val-Dil-Dap-Ile-OCH$_3$ (3d)

Chromatographic separation on a SILICA GEL column with 1:2 hexane-acetone as the eluent gave the required pentapeptide as colorless powder (3d, 80%); m.p.=80°–82° C.; $[\alpha]_D^{25}$=–39.3° (c 0.14, CHCl$_3$); IR(thin film): 3300, 3050, 2965, 2878, 2830, 2787, 1746, 1622, 1530, 1454, 1383, 1267, 1120, 1099, 1038 and 735; MS: m/z 725(M$^+$), 682, 481, 399, 227, 186, 170, 154 and 128. Anal. Found: C: 63.03, H: 10.01, N: 9.77. C$_{38}$H$_{71}$N$_5$O$_8$ requires C: 62.86, H: 9.86, N: 9.65.

Dov-Val-Dil-Dap-Met-OCH$_3$ (3e)

Chromatographic separation using a SILICA GEL column with 1:2 hexane-acetone as the eluent resulted in the required pentapeptide as colorless powder (3e, 78%); m.p.= 63°–65° C.; $[\alpha]_D^{25}$=–44.1° (c, 0.44, CHCl$_3$); IR(thin film): 3297, 2963, 2934, 2876, 2830, 2787, 1750, 1620(br), 1539, 1449, 1420, 1375, 1198 and 1098; MS (m/z): 743 (M$^+$), 700, 611, 568, 481, 417, 311, 227 and 154. Anal. Found: C: 59.78, H: 9.14, N: 9.16, S: 4.39. C$_{37}$H$_{69}$N$_5$O$_{68}$S requires C: 59.73, H: 9.35, N: 9.41, S: 4.31.

To further aid in the understanding of the present invention, and not by way of limitation, the following examples are presented.

EXAMPLE Ia
Synthesis of Boc-Dap-Phe-OCH$_3$ (1a)

The general procedure for the synthesis of dipeptides (1a–1e) was followed. The numerical identificate shown in Scheme 1 is followed herein. Chromatographic separation on a SILICA GEL column with 3:1 hexane-acetone as the eluent resulted in the required dipeptide as a thick oil. Crystallization from ether-hexane gave sparkling crystals of the pure compound (1a, 96%); m.p.=125° C.; $[\alpha]_D^{25}$=–15.1 (c 0.41, CHCl$_3$); IR(thin film): 3314, 2974, 2934, 2878, 1748, 1692, 1663, 1537, 1456, 1400, 1366, 1173, 1101 and 700; $^1$H NMR (300 MHz, CDCl$_3$): 1.163(d, J=7.0 Hz, 3H, CH$_3$), 1.4816(s, 9H, t-Bu), 1.624–1.850(m, 4H, 2×CH$_2$), 2.25–2.45(m, 1H, CHCO), 3.045(dd, J=13.9 and 7.8 Hz, 1H, ½ CH$_2$—Ph), 3.175(dd, J=13.8 and 5.55 Hz, 1H, ½ CH$_2$—Ph), 3.3642(s, 3H, OCH$_3$), 3.3701(s, 3H, OCH$_3$), 3.50–3.60 (m, 1H, CH—OCH$_3$), 3.7422(m, 2H, CH$_2$—N), 3.85(m, 1H, pro CH—N), 4.80(m, 1H, phe CH—N), 6.10, 6.75(m, 1H, NH) and 7.10–7.32(m, 5H, Ph); MS: m/z 416(M—MeOH), 375, 316, 264, 210, 170, 114(100%) and 70. Anal. Found: H: 8.12, N: 6.20. C$_{24}$H$_{36}$N$_2$O$_6$ requires H: 8.09, N: 6.25.

EXAMPLE Ib
Synthesis of Boc-Dap-Phe-NH$_2$ (1b)

The general procedure for the synthesis of dipeptides (1a–1e) was followed. Chromatographic purification using a SILICA GEL column with 1:1 hexane-acetone as the eluent gave the required dipeptide as a crystalline solid. Recrystallization from acetone gave sparkling crystals of the pure compound (1b, 65%); m.p.=199°–200° C. (acetone); $[\alpha]_D^{25}$=–40 (c 0.15, CHCl$_3$); IR(thin film): 3302, 3198, 2974, 2934, 2878, 1669, 1539, 1456, 1404, 1366, 1169, 1111 and 700; $^1$H NMR (300 MHz, CDCl$_3$): 1.019(brs, 3H, CH$_3$), 1.426(s, 9H, t-Bu), 1.55–1.90(m, 4H, 2×CH$_2$), 2.30(quintet, 1H, CH—CO), 3.00–3.25(m, 3H, CH$_2$—N, CH—OCH$_3$), 3.349(s, 3H, OCH$_3$), 3.60–3.75(m, 1H, pro CH—N), 4.60–4.80(m, 1H, phe CH—N), 5.30(brs, 1H, NH), 6.287(d, J=7.2 Hz, 1H, NH), 6.90(brm, 1H, NH) and 7.164–7.306(m, 5H, C$_6$H$_5$); MS: m/z 433(M$^+$), 401(M—MeOH), 360, 301, 247, 232, 210, 170, 154, 138, 114 and 70(100%). Anal. Found: C: 63.75, H:8.18, N: 9.62. C$_{23}$H$_{35}$N$_3$O$_5$ requires C: 63.72, H: 8.14, N: 9.69.

EXAMPLE Ic
Synthesis of Boc-Dap-Pro-OCH$_3$ (1c)

The general procedure for the synthesis of dipeptides was followed. Chromatographic separation on a SILICA GEL column with 3:2 hexane-acetone as the eluent gave the required dipeptide as a thick oil (1c, 92%); $[\alpha]_D^{25}$=–101.5 (c 0.2, CHCl$_3$); IR(neat): 2974, 2880, 1748, 1692, 1647, 1398, 1366, 1171 and 1098; $^1$H NMR (300 MHz, CDCl$_3$): 1.222(d, J=7.0 Hz, 3H, CH$_3$), 1.440(s, 9H, t-Bu), 1.65–2.20(m, 8H, 4×CH$_2$), 2.60–2.70(m, 1H, CH—CO), 3.10–3.22(m, 1H, CH—OCH$_3$), 3.417(s, 3H, CH$_3$), 3.45–3.65(m, 4H, 2×CH$_2$—N), 3.675(s, 3H, OCH$_3$), 3.74–3.83(m, 1H, CH—N) and 4.447(dd, J=8.55 and 3.5 Hz, 1H, CH—COOCH$_3$). HRFABMS: m/z 399.24880(M+H)$^+$; [C$_{20}$H$_{35}$N$_2$O$_6$]$^+$ requires 399.24951.

EXAMPLE Id
Synthesis of Boc-Dap-Ile-OCH$_3$ (1d)

The general procedure for the synthesis of dipeptides (1a–1e) was followed. Chromatographic purification on a SILICA GEL column with 3:2 hexane-ethyl acetate as the eluent yielded the required dipeptide as an oily liquid (1d, 72%); m.p.=76°–77° C. (acetone); $[\alpha]_D^{25}$=–28.2 (c 0.17, CHCl$_3$); IR(thin film): 3325, 2971, 2936, 2878, 1746, 1694, 1667, 1530, 1478, 1398, 1254, 1175, 1105, 868 and 774; $^1$H NMR (300 MHz, CDCl$_3$): 0.882(d, J=6.9 Hz, 3H, CH$_3$—CH), 0.9012(t, J=7.4 Hz, 3H, CH$_3$—CH$_2$), 1.05–1.24 (m, 5H, CH$_3$, CH$_2$—CH$_3$), 1.4526(s, 9H, t-Bu), 1.65–2.00 (m, 5H, 2×CH$_2$, CH—CH$_2$), 2.30–2.50(m 1H, CH—CO), 3.18–3.28(m, 1H, CH—OCH$_3$), 3.422(s, 3H, OCH$_3$), 3.48–3.60(m, 1H, pro CH—N), 3.699(s, 3H, OCH$_3$), 3.72–3.82(m, 1H, ½ CH$_2$—N), 3.88–3.98(m, 1H, ½ CH$_2$—N, 4.44–4.58(m, 1H, ile CH—N) and 6.15, 6.7(m, 1H, NH); MS: m/z 382(M—MeOH), 341, 282, 245, 230, 210, 170, 114, 70(100%) and 57. Anal. Found: C: 61.06, H: 9.25, N: 6.64. C$_{21}$H$_{38}$N$_2$O$_6$ requires C: 60.84, H: 9.24, N: 6.76.

EXAMPLE Ie
Synthesis of Boc-Dap-Met-OCH$_3$ (1e)

The general procedure for the synthesis of dipeptides (1a–1e) was followed. Chromatographic separation on a SILICA GEL column using 3:2 hexane-acetone as the eluent gave the required dipeptide as a solid (1e, 83%); m.p.= 68°–70° C.; $|\alpha|_D^{25}$=−27.6 (c, 0.59, CHCl$_3$ $_{IR(neat)}$: 3312, 2974, 2934, 2878, 1748, 1692, 1663, 1539, 1398, 1366, 1256, 1171, 1115, 866 and 774; $^1$H NMR (CDCl$_3$): 1.223 (brs, 3H, CH—CH$_3$), 1.441(brs, 9H, t-Bu), 1.6–1.2(m, 6H, 3×CH$_2$), 2.070 (s, 3H, S—CH$_3$), 2.3–2.55(m, 3H, CH$_2$—S, CH—CO), 3.15–3.35 (m, 2H, N—CH$_2$), 3.420 (s, 3H, OCH$_3$), 3.55(m, 1H, CH—OCH$_3$), 3.716(brs, 3H, COOCH$_3$), 3.85–4.0(m, 1H, pro CH—N), 4.6(brm, 1H, met CH—N), 6.3(brm, 1H, NH); MS (m/z): 432 (M$^+$), 400, 359, 258, 210, 170, 114(100%). Anal. Found: C: 55.35, H: 8.33, N: 6.53, S: 7.23. C$_{20}$H$_{36}$N$_2$O$_6$ S requires C: 55.53, H: 8.39, N: 6.48, S: 7.41.

EXAMPLE IIa
Synthesis of Dap-Phe-OCH$_3$ Tfa (2a)

General procedure A was followed. After removing toluene under reduced pressure, the residue obtained as a thick oily mass was titrated with ether to obtain the trifluoroacetate salt (2a, quantitative) as a colorless crystalline solid: IR(thin film): 3275, 2928, 1744, 1674, 1541, 1456, 1202, 1132 and 721; $^1$H NMR (300 MHz, CDCl$_3$): 1.107(brs, 3H, CH$_3$), 1.60–2.10(m, 4H, 2×CH$_2$), 2.60(m, 1H, CHCO), 2.90–3.00(m, 2H, CH$_2$—Ph), 3.10–3.35(m, 3H, CH—OCH$_3$, CH$_2$—N), 3.209(s, 3H, OCH$_3$), 3.40–3.55(m, 1H, pro CH—N), 3.712(s, 3H, COOCH$_3$), 4.75(m, 1H, phe CH—N), 7.106(m, 1H, NH), 7.124–7.324(m, 5H, Ph) and 8.7(m, 1H, NH); HRFABMS: m/z 349.21350(100%, cation); |C$_{19}$H$_{29}$N$_2$O$_4$|$^+$ requires 349.21273.

EXAMPLE IIb
Synthesis of Dap-Phe-NH$_2$ Tfa (2b)

General procedure A was followed. Removal of toluene under reduced pressure left the trifluoroacetate salt (2b, 97%) as a colorless solid.

EXAMPLE IIc
Synthesis of Dap-Pro-OCH$_3$ Tfa (2c)

General procedure A was followed. After removing toluene under reduced pressure, residue obtained as a thick oily mass was triturated with ether to obtain the trifluoroacetate salt (2c, 99%) as a colorless crystalline solid: IR(thin film): 2980, 2890, 1746, 1680, 1626, 1437, 1287, 1200, 1094, 799 and 721; $^1$H NMR (300 MHz, CDCl$_3$): 1.307(d, J=6.9 Hz, 3H, CH$_3$), 1.85–2.30(m, 8H, 4×CH$_2$) 2.85(m, 1H, CH—CO), 3.20–3.40(m, 1H, CH—OCH$_3$), 3.485(s, 3H, CH$_3$), 3.35–3.75(m, 3H, CH—N, CH$_2$—N), 3.687(s, 3H, COOCH$_3$), 4.165(m, 2H, CH$_2$—N$^+$), 4.442(m, 1H, CH—N$^+$) and 8.008(m, NH). HRFABMS: m/z 299.19770 (100%, cation); |C$_{15}$H$_{27}$N$_2$O$_4$|$^+$ requires 299.1971.

EXAMPLE IId
Synthesis of Dap-Ile-OCH$_3$ Tfa (2d)

General procedure A was followed. After removing toluene under reduced pressure, the residue obtained as a thick oily mass was triturated with ether to obtain the trifluoroacetate salt (2d, 97%) as a gummy mass; IR(thin film): 3289, 2969, 2884, 1744, 1674, 1541, 1458, 1383, 1202, 1136, 833, 799 and 721; $^1$H NMR (300 MHz, CDCl$_3$): 0.88(brs, 3H, CH$_3$), 1.884(t, J=6.7 Hz, 3H, CH$_3$—CH$_2$), 1.209(d, J=6.8 Hz, CH$_3$—CH), 1.10–1.50(m, 2H, CH$_2$), 1.80–2.20(m, 5H, 2×CH$_2$, CH$_3$—CH), 2.707(m, 1H, CH—CO), 3.10–3.41(m, 2H, CH$_2$—N), 3.470(s, 3H, OCH$_3$), 3.60–3.70(M, 1H, CH—OCH$_3$), 3.85–3.90(m, 1H, pro CH—N), 3.702(s, 3H, COOCH$_3$), 4.43(dd, J=7.5 and 5.4 Hz, 1H, ile CH—N), 6.926(d, J=7.9 Hz, 1H, NH), 8.8(m, 1H, ½ NH$_2$) and 10(m, 1H, ½ NH$_2$); MS: HRFAB: m/z 315.22890(100%, cation); |C$_{16}$H$_{31}$N$_2$O$_4$|$^+$ requires 315.22838.

EXAMPLE IIe
Synthesis of Dap-Met-OCH$_3$ Tfa (2e)

General procedure A was followed. Removal of toluene under reduced pressure left the trifluoroacetate salt (2e, quantitative) as a gummy mass.

EXAMPLE IIIa
Synthesis of Dov-Val-Dil-Dap-Phe-OCH$_3$ (3a)

Chromatographic separation on a SILICA GEL column with 3:4 hexane-acetone as the eluent gave the required pentapeptide(3a, 87%); m.p.=80°–83° C.; $|\alpha|_D^{25}$=−35.3 (c 0.34, CHCl$_3$); IR(thin film): 3298, 2963, 2934, 2876, 2830, 2787, 1748, 1622, 1532, 1454, 1379, 1269, 1200, 1099, 1038, 737 and 700; MS: m/z 759(M$^+$), 716, 481, 449, 433, 227, 186, 154, 128, 100(100%), 85 and 70. Anal. Found: C: 64.91, H: 9.33, N: 8.97. C$_{41}$H$_{69}$N$_5$O$_8$ requires C: 64.71, H: 9.15, N: 9.22.

EXAMPLE IIIb
Synthesis of Dov-Val-Dil-Dap-Phe-NH$_2$ (3b)

General procedure B was followed. Chromatographic separation on a SILICA GEL column with 1:3 hexane-acetone as the eluent resulted in the required pentapeptide as colorless powder (3b, 99%); m.p.=111°–113° C.; $|\alpha|_D^{25}$=−42 (c 0.25, CHCl$_3$); IR(thin film): 3304, 3138, 3054, 2965, 2934, 2876, 2830, 2787, 1622, 1541, 1499, 1423, 1371, 1306, 1252, 1202, 1171, 1098, 1038, 756, 735 and 696; MS: m/z 744(M$^+$), 701, 669, 519, 481, 418, 227, 206, 186, 170, 154, 128 and 114.

EXAMPLE IIIc
Synthesis of Dov-Val-Dil-Dap-Pro-OCH$_3$ (3c)

General procedure B was followed. Chromatographic purification using a SILICA GEL column with 1:3 hexane-acetone as the eluent yielded the required pentapeptide as colorless powder (3c, 69%); m.p.=75°–77° C.; $|\alpha|_D^{25}$=−52.7 (c 0.11, CHCl$_3$); IR(thin film): 3293, 2963, 2876, 2830, 2789, 1750, 1624, 1422, 1385, 1273, 1198, 1096, 1040 and 733; MS: m/z 709(M$^+$), 666, 581, 481, 449, 412, 383, 369, 297, 255, 227(100%), 199, 186, 170 and 155. Anal. Found: C: 62.51, H: 9.61, N: 9.72. C$_{37}$H$_{67}$N$_5$O$_8$ requires C: 62.59, H: 9.51, N: 9.87.

EXAMPLE IIId
Synthesis of Dov-Val-Dil-Dap-Ile-OCH$_3$ (3d)

General procedure B was followed. Chromatographic separation on a SILICA GEL column with 1:2 hexane-acetone as the eluent gave the required pentapeptide as colorless powder (3d, 80%); m.p.=80°–82° C.; $|\alpha|_D^{25}$=−39.3 (c 0.14, CHCl$_3$); IR(thin film): 3300, 3050, 2965, 2878, 2830, 2787, 1746, 1622, 1530, 1454, 1383, 1267, 1120, 1099, 1038 and 735; MS: m/z 725(M$^+$), 682, 481, 399, 227, 186, 170, 154 and 128. Anal. Found: C: 63.03, H: 10.01, N: 9.77. C$_{38}$H$_{71}$N$_5$O$_8$ requires C: 62.86, H: 9.86, N: 9.65.

EXAMPLE IIIe
Synthesis of Dov-Val-Dil-Dap-Met-OCH$_3$ (3e)

General procedure B was followed. Chromatographic separation using a SILICA GEL column with 1:2 hexane-acetone as the eluent resulted in the required pentapeptide as colorless powder (3e, 78%); m.p.=63°–65° C.; $|\alpha|_D^{25}$=−44.1 (c, 0.44, CHCl$_3$); IR (thin film): 3297, 2963, 2934, 2876, 2830, 2787, 1750, 1620(br), 1539, 1449, 1420, 1375, 1198 and 1098; MS (m/z): 743 (M⁺), 700, 611, 568, 481, 417, 311, 227 and 154. Anal. Found: C: 59.78, H: 9.14, N: 9.16, S: 4.39. $C_{37}H_{69}N_5O_{68}S$ requires C: 59.73, H: 9.35, N: 9.41, S: 4.31.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

---

What is claimed:

1. A composition of matter having the structural formula designated 3(a-e):

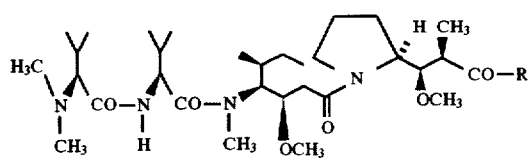

wherein R is selected from the following group of substituents:

a)

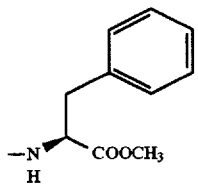

b)

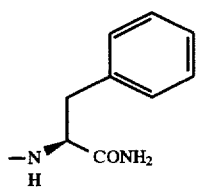

c)

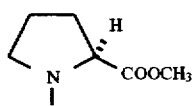

d)

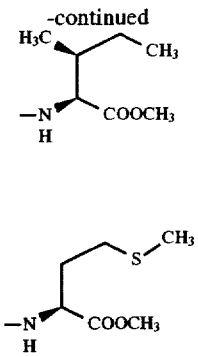

e)

2. A composition of matter according to claim 1 in which R is the substituent designated a.

3. A composition of matter according to claim 1 in which R is the substituent designated b.

4. A composition of matter according to claim 1 in which R is the substituent designated c.

5. A composition of matter according to claim 1 in which R is the substituent designated d.

6. A composition of matter according to claim 1 in which R is the substituent designated e.

7. A method for inhibiting the growth of human cancer cells wherein said cancer is selected from the group consisting of leukemia, ovarian cancer, CNS cancer, mammary cancer, non-small cell lung cancer, renal cancer, colon cancer, and melanoma consisting of administering an active ingredient selected from the group consisting of: Dov-Val-Dil-Dap-Phe-$OCH_3$, Dov-Val-Dil-Dap-Phe-$NH_2$, Dov-Val-Dil-Dap-Pro-$OCH_3$, Dov-Val-Dil-Dap-Ile-$OCH_3$, and Dov-Val-Dil-Dap-Met-$OCH_3$, to said cells in a quantity sufficient to inhibit the growth of said cells.

8. A method according to claim 7 wherein said active ingredient consists of Dov-Val-Dil-Dap-Phe-$OCH_3$.

9. A method according to claim 7 wherein said active ingredient consists of Dov-Val-Dil-Dap-Phe-$NH_2$.

10. A method according to claim 7 wherein said active ingredient consists of Dov-Val-Dil-Dap-Pro-$OCH_3$.

11. A method according to claim 7 wherein said active ingredient consists of Dov-Val-Dil-Dap-Ile-$OCH_3$.

12. A method according to claim 7 wherein said active ingredient consists of Dov-Val-Dil-Dap-Met-$OCH_3$.

13. A method according to claim 7 for inhibiting the growth of human cancer cells selected from the group of cell lines consisting of P388 Lymphotic Leukemia, L1210 Lymphatic Leukemia, B16 Melanoma, M5076 Ovary Sarcoma, LOX Human Melanoma, Human Mammary MX-7, and OVCAR-3, consisting of administering an active ingredient selected from the group consisting of Dov-Val-Dil-Dap-Phe-OCH$_3$, Dov-Val-Dil-Dap-Phe-NH$_2$, Dov-Val-Dil-Dap-Pro-OCH$_3$, Dov-Val-Dil-Dap-Ile-OCH$_3$, and Dov-Val-Dil-Dap-Met-OCH$_3$, to said cells in a quantity sufficient to inhibit the growth of said cells.

14. A method according to claim 7 wherein said cancer is selected from the group of cell lines consisting of P388, OVCAR-3, SF-295, A498, NCI-H460, KM20L2, and SK-MEL-3.

15. A method according to claim 14 wherein said active ingredient consists of Dov-Val-Dil-Dap-Phe-OCH$_3$.

16. A method according to claim 14 wherein said active ingredient consists of Dov-Val-Dil-Dap-Phe-NH$_2$.

17. A method according to claim 14 wherein said active ingredient consists of Dov-Val-Dil-Dap-Pro-OCH$_3$.

18. A method according to claim 14 wherein said active ingredient consists of Dov-Val-Dil-Dap-Ile-OCH$_3$.

19. A method according to claim 14 wherein said active ingredient consists of Dov-Val-Dil-Dap-Met-OCH$_3$.

* * * * *